US009333293B2

(12) United States Patent
Williams, Jr. et al.

(10) Patent No.: US 9,333,293 B2
(45) Date of Patent: May 10, 2016

(54) INJECTOR DEVICE, METHOD, AND COMPUTER PROGRAM PRODUCT FOR DETECTING A VACUUM WITHIN A SYRINGE

(75) Inventors: Robert C. Williams, Jr., Fort Salonga, NY (US); Alan Cross-Hansen, Massapequa Park, NY (US)

(73) Assignee: ACIST Medical Systems, Inc., Eden Prairie, MN (US)

(*) Notice: Subject to any disclaimer, the term of this patent is extended or adjusted under 35 U.S.C. 154(b) by 1983 days.

(21) Appl. No.: 11/746,298

(22) Filed: May 9, 2007

(65) Prior Publication Data

US 2008/0281278 A1 Nov. 13, 2008

(51) Int. Cl.
*A61M 5/145* (2006.01)
*A61M 5/20* (2006.01)
*A61M 5/168* (2006.01)

(52) U.S. Cl.
CPC ....... *A61M 5/14526* (2013.01); *A61M 5/16854* (2013.01); *A61M 5/20* (2013.01); *A61M 5/14566* (2013.01); *A61M 2205/18* (2013.01); *A61M 2205/332* (2013.01); *A61M 2205/3331* (2013.01)

(58) Field of Classification Search
CPC ............... A61M 2005/14573; A61M 5/20; F04B 13/00; F04B 2205/03; F04B 43/04; Y10T 403/10; Y10T 403/551
USPC ............... 604/65–67, 154, 155, 503, 505
See application file for complete search history.

(56) References Cited

U.S. PATENT DOCUMENTS

| | | | |
|---|---|---|---|
| 3,523,523 A | 8/1970 | Reich et al. | |
| 3,623,474 A * | 11/1971 | Heilman | A61M 5/14546 600/432 |
| 3,701,345 A | 10/1972 | Heilman et al. | |
| 4,869,720 A | 9/1989 | Chernack | |
| 5,672,155 A * | 9/1997 | Riley et al. | 604/154 |
| 5,853,665 A * | 12/1998 | Ade | G01N 35/1079 422/112 |
| 5,894,273 A * | 4/1999 | Meador et al. | 340/606 |
| 5,957,950 A * | 9/1999 | Mockros | A61M 25/104 600/586 |
| 6,159,181 A * | 12/2000 | Crossman | A61M 5/2033 604/134 |
| 6,362,591 B1 * | 3/2002 | Moberg | 318/685 |
| 6,387,078 B1 * | 5/2002 | Gillespie, III | A61M 5/2066 604/181 |

(Continued)

FOREIGN PATENT DOCUMENTS

EP      1 186 311 A2    3/2002
WO    WO-02/22190 AI    3/2002

OTHER PUBLICATIONS

The International Search Report and Written Opinion for International Application No. PCT/US2008/062801, mailed Aug. 6, 2008.

*Primary Examiner* — Kami A Bosworth
*Assistant Examiner* — Matthew A Engel
(74) *Attorney, Agent, or Firm* — Fredrikson & Byron, P.A.

(57) ABSTRACT

An injector system, method and computer program product for detecting a vacuum within a syringe are provided. Various embodiments include an actuator device configured to be engaged with a piston member of a syringe for extending and retracting the piston member within the syringe. A controller device is also provided for detecting an output generated by the actuator device when retracting the piston member. The detected output may be associated with a pressure within the reservoir. The controller device determines, via the detected output, when the pressure comprises a selected negative pressure and provides an indicia of the negative pressure to a user and/or a signal to the actuator device.

9 Claims, 8 Drawing Sheets

(56) References Cited

U.S. PATENT DOCUMENTS

| | | | |
|---|---|---|---|
| 6,409,696 B1 * | 6/2002 | Toavs et al. | 604/6.01 |
| 6,673,033 B1 | 1/2004 | Sciulli et al. | |
| 6,742,993 B2 * | 6/2004 | Savard | F04B 7/0266 222/61 |
| 7,087,033 B2 * | 8/2006 | Brugger | A61M 1/3626 604/4.01 |
| 8,608,665 B2 * | 12/2013 | Vad | A61B 17/3401 340/573.1 |
| 2002/0120236 A1 * | 8/2002 | Diaz | A61M 5/14216 604/151 |
| 2002/0183616 A1 * | 12/2002 | Toews | A61M 5/007 600/432 |
| 2002/0198494 A1 * | 12/2002 | Diaz | A61M 5/14216 604/131 |
| 2004/0024367 A1 * | 2/2004 | Gilbert | A61M 5/2033 604/198 |
| 2004/0064041 A1 * | 4/2004 | Lazzaro | A61M 5/14546 600/432 |
| 2005/0113754 A1 * | 5/2005 | Cowan | A61M 5/14546 604/131 |
| 2006/0079768 A1 | 4/2006 | Small et al. | |
| 2006/0089544 A1 * | 4/2006 | Williams, Jr. | G06F 19/3406 600/300 |
| 2006/0178616 A1 * | 8/2006 | Hartman | G01N 23/04 604/65 |
| 2008/0004507 A1 * | 1/2008 | Williams, Jr. | A61B 5/00 600/300 |
| 2008/0053560 A1 * | 3/2008 | Hartman | B65B 3/003 141/2 |
| 2008/0281278 A1 * | 11/2008 | Williams, Jr. | A61M 5/14526 604/264 |
| 2009/0214094 A1 * | 8/2009 | Williams | A61B 6/481 382/131 |
| 2014/0350510 A1 * | 11/2014 | Carlisle | A61M 5/155 604/500 |

* cited by examiner

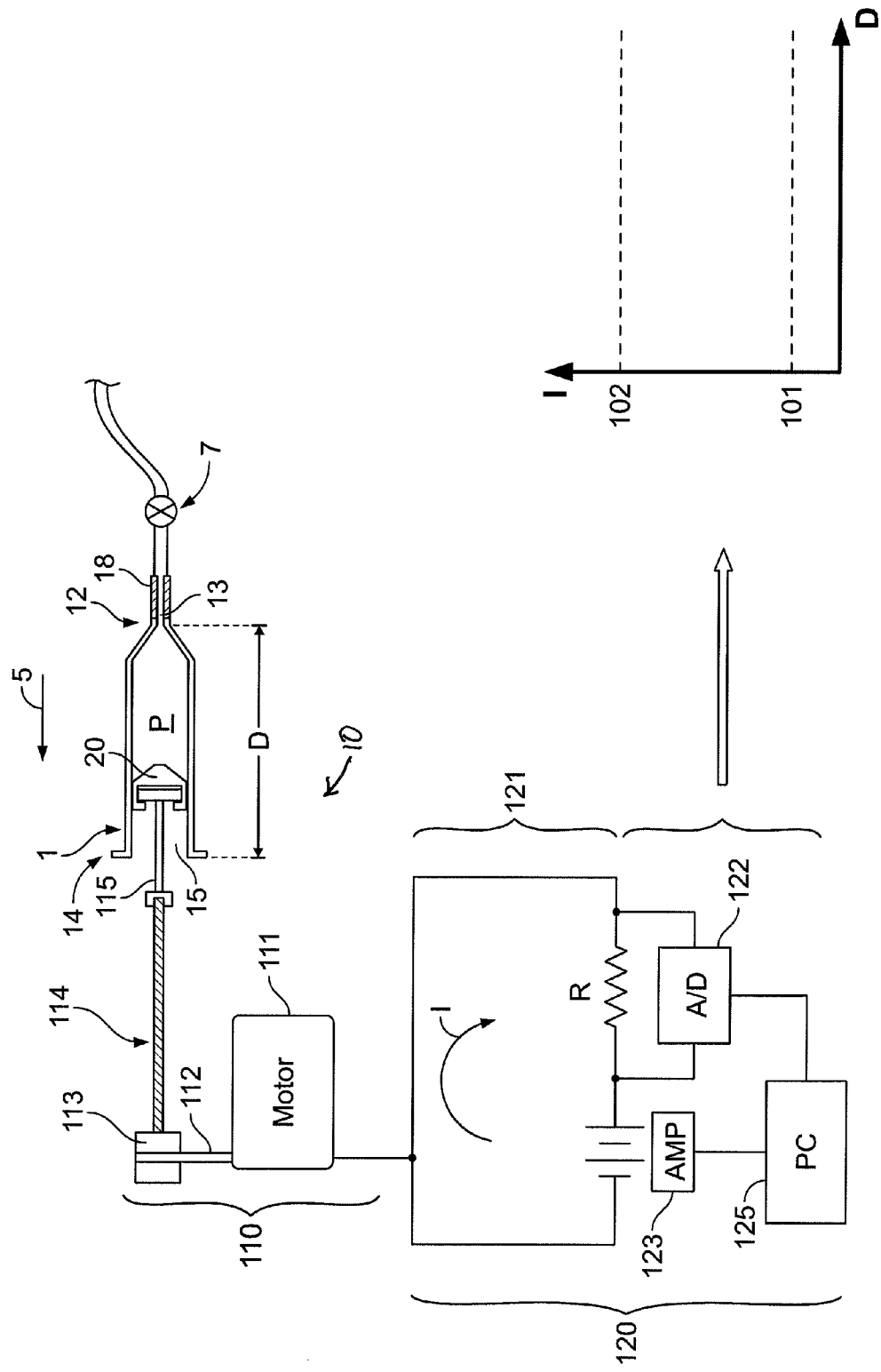

INJECTOR DEVICE, METHOD, AND COMPUTER PROGRAM PRODUCT FOR DETECTING A VACUUM WITHIN A SYRINGE

FIELD OF THE INVENTION

The various embodiments of the present invention relate to the field of injector devices adapted to be operably engaged with a syringe device, to dispense therapeutic and/or diagnostic agents to a subject. More particularly, the various embodiments of the present invention provide an injector device and method capable of preventing potentially hazardous piston recoils, ingress of air and/or formation of vapor in syringe devices by detecting the presence of a vacuum within the syringe device and alerting a user accordingly.

BACKGROUND OF THE INVENTION

Syringe devices, such as those adapted to be operably engaged with conventional power injector devices, are designed to provide metered amounts of a particular therapeutic and/or diagnostic compound to a patient via needle and/or other conduit that may be operably engaged with a distal end of the syringe device. Such syringe devices provide a piston assembly that is movable between a distal end of the syringe device and a proximal end of the syringe device. Because the piston assembly is often engaged with an interior sidewall of the syringe reservoir in a substantially air-tight engagement (via one or more wiper seals, for example), the retraction of the piston assembly (by a plunger actuated by the power injector device, for example), towards the proximal end of the syringe assembly may generate a substantial vacuum within the syringe assembly. The generation of a vacuum within a syringe assembly may be caused, for example, when a distal aperture (and/or a conduit downstream of such a distal aperture) defined in the syringe device, is partially or completely occluded (in some cases, by a closed check valve disposed downstream of the distal end of the syringe device).

For example, in some conventional injector devices, a disposable syringe device may be operably engaged with the injector device. The injector device may be capable of automatically retracting the piston assembly to a "replace syringe" position near a proximal end of the syringe device such that the syringe device may be removable from the injector device to facilitate disposal and/or replacement of the disposable syringe device. In some such conventional injector devices, the movement of the piston assembly to the "replace syringe" position causes a plunger of the injector device to disengage from the piston assembly when the piston assembly reaches the proximal end of the syringe assembly. Thus, if a substantial vacuum has been created in the syringe device, the force of the vacuum may rapidly (and sometimes violently) draw the piston assembly towards the distal end of the syringe assembly when the power injector device disengages the piston assembly. The resulting "piston slap" may, in turn, be violent enough to crack and/or shatter a portion of the syringe device. Furthermore, the generation of a negative pressure within the syringe may also be indicative of a retraction of the piston assembly which may, in some cases, cause air to be drawn into the syringe or vapor to form from any liquid content in the syringe. The resulting air bubbles may be hazardous if injected into the bloodstream of a patient via the distal aperture of the syringe. Furthermore, some injector devices may be capable of being operably engaged with multiple syringe devices that may be in fluid communication via a manifold (or a plurality of check valves) leading to a central line leading to a patient. Thus, the generation of a negative pressure in one or more of the syringe devices may be indicative of a commingling of fluids introduced via the syringes. Such commingling may cause cross-contamination and/or compromise the sterility of some reusable components of an injector system. Therefore, for at least the reasons cited herein, it may be technically advantageous to detect a selected level of negative pressure within one or more syringe devices and alert a user of the injector device if and when such a negative pressure is detected.

Some conventional power injector devices include monitoring systems in communication with a controller that drives the plunger assembly for detecting a positive pressure in the syringe during an extension cycle (so as to be capable of delivering a dose of a particular therapeutic and/or diagnostic compound to a patient at a substantially constant flow rate). Furthermore, such conventional systems are configured for monitoring the electrical current in an injector device during the forward or "extension" movement and providing feedback to a control circuit in order to ensure that the dispensing flow rate is relatively constant over the length of the dispensing stroke. However, such conventional systems are not capable of detecting the presence of a selected negative pressure that may be produced during a retraction cycle. Furthermore, such conventional systems are unsuitable for detecting a characteristic a pressure build-up on the "retract" side of a hydraulic actuator (that may be used, for example, in a magnetic resonance imaging (MRI) suite in lieu of an electrically-powered injector), that may be indicative of a negative pressure within a syringe. Thus, conventional injector devices may be incapable of detecting and/or preventing an imminent "piston slap" incident during a retraction cycle in both electrically-powered and hydraulically-powered injector devices. Furthermore, such conventional power injector devices do not include controller logic that may allow for the automatic shutdown of the injector device in cases where a selected negative pressure is detected in a syringe during a retract cycle.

Thus, there exists a need in the art for an injector device that is capable of detecting and quantifying a negative pressure (or vacuum) generated in a conventional syringe device when a distal end of the syringe device is occluded during retraction of the piston assembly within the syringe. There further exists a need in the art for an injector device, method, and computer program product that is capable of correlating at least one of an electrical current drawn by an electrically-powered actuator and a hydraulic pressure within a hydraulically-powered actuator, to a negative pressure produced in a syringe during a retraction cycle of the injector device. There further exists a need in the art for an injector device capable of automatically shutting down in response to a detected negative pressure and/or alerting a user of a detected negative pressure produced within a syringe during a retraction cycle. Finally, there exists a need in the art for an injector system that allows for a user to specify a selected negative pressure which, when detected, triggers an automatic shutdown of the injector device and/or the generation of an alert signal that may be perceptible to a user of the device.

BRIEF SUMMARY OF THE INVENTION

The needs outlined above and others are met by the present invention which, in various embodiments, provides various injector device, method, and computer program product embodiments that overcome many of the technical problems discussed above. Specifically, in one embodiment, the injector device is adapted to be operably engaged with a syringe device comprising a reservoir including a dispensing distal end defining a dispensing aperture and a proximal end defining a proximal aperture. The syringe device may further comprise a piston member movably disposed in the reservoir and configured to be movable between the distal end and the proximal end. Furthermore, the piston member may be in movable sealing engagement with a reservoir sidewall. In one embodiment, the injector system comprises an actuator device configured to be selectively operably engaged with the piston member for extending the piston member toward the distal end and retracting the piston member toward the proximal end. Furthermore, the injector device may further comprise a controller device in communication with the actuator device. The controller device may be configured to detect an output generated by the actuator device when retracting the piston member, wherein the output is associated with a pressure within the reservoir. The controller device may be further configured to determine, via the detected output, when the pressure comprises a selected negative pressure. Furthermore, the controller device may be configured to provide indicia of the selected negative pressure to a user, or a signal of the selected negative pressure to the actuator device, in response to the determined selected negative pressure. In some embodiments, the controller device may be further configured to convert the output into a pressure value comparable to the selected negative pressure.

In one embodiment, the actuator device may comprise an electric motor operably engaged with a movable plunger head configured to be selectively operably engaged with the piston member for extending the piston member toward the distal end and retracting the piston member toward the proximal end. According to such embodiments, the output of the actuator device may comprise an electrical current drawn by the actuator device when retracting the piston member. In such embodiments, the controller device may comprise an electrical sensor configured to determine when the pressure comprises the selected negative pressure based at least in part on the electrical current drawn by the actuator device when retracting the piston member.

In another embodiment, the actuator device may comprise a hydraulic servo system comprising a hydraulic actuator for extending the piston member toward the distal end and retracting the piston member toward the proximal end. According to such embodiments, the output of the actuator device may comprise a hydraulic pressure within the hydraulic actuator when retracting the piston member. Furthermore, in such embodiments, the controller device may comprise a pressure transducer device configured to determine when the pressure comprises the selected negative pressure based at least in part on the hydraulic pressure within the hydraulic actuator when retracting the piston member.

According to some embodiments, the injector system may further comprise a user interface in communication with the controller device. According to such embodiments, the controller device may be configured to provide indicia of the selected negative pressure to a user via the user interface in the form of a perceptible output transmitted via the user interface. For example, in one embodiment, the user interface may comprise a speaker and the perceptible output may comprise an audible alarm. In other embodiments, the user interface may comprise a display and the perceptible output may comprise a visible indicia shown on the display. According to some such embodiments, the visible indicia may comprise a prompt to clear an obstruction in a conduit in fluid communication with, and disposed distally from, the dispensing aperture of the syringe device. In such embodiments, the prompt may include, but is not limited to text instructions and a pictogram. Some injector system embodiments may further comprise a user interface configured to receive a threshold value corresponding to the selected negative pressure such that a user may specify the selected negative pressure at which the controller device provides the indicia of the selected negative pressure to a user, or at which the controller device provides a signal of the selected negative pressure to the actuator device. In some embodiments, the actuator device may be configured to automatically cease extending the piston member toward the distal end or retracting the piston member toward the proximal end in response to the signal provided by the controller device.

Methods and corresponding computer program product embodiments are also provided for detecting a substantially negative pressure in a syringe device. As described herein, such syringe devices may comprise a reservoir including a dispensing distal end defining a dispensing aperture and a proximal end defining a proximal aperture. Furthermore, the syringe device may further comprise a piston member movably disposed in the reservoir and configured to be movable between the distal end and the proximal end, wherein the piston member is in movable sealing engagement with a reservoir sidewall. Some method and/or computer program product embodiments comprise steps for moving the piston member using an actuator device configured to be selectively operably engaged with the piston member for extending the piston member toward the distal end and retracting the piston member toward the proximal end, and detecting an output generated by the actuator device when retracting the movable plunger head. As described herein, the detected output may be associated with a pressure within the reservoir. Various method and/or computer program product embodiments may further comprise steps for determining, via the detected output, when the pressure comprises a selected negative pressure, and providing an indicia of the determined selected negative pressure to a user or a signal thereof to the actuator device.

Some method and/or computer program product embodiments may allow for a user-defined selected negative pressure. For example, such embodiments may further comprise a step for comprising receiving a threshold value corresponding to the selected negative pressure. In some method and/or computer program product embodiments, the method may comprise a step for converting the output into a pressure value that is substantially comparable to the selected negative pressure. Furthermore, according to some embodiments, the method and/or computer program product may further comprise ceasing extension of the piston member toward the distal end and/or ceasing retraction of the piston member toward the proximal end in response to the signal provided in the providing step.

As described herein, the actuator device may comprise an electric motor operably engaged with a movable plunger head configured to be selectively operably engaged with the piston member for extending the piston member toward the distal end and retracting the piston member toward the proximal end. In such embodiments, the output of the actuator device may comprise an electrical current drawn by the actuator device when retracting the piston member. According to such embodiments, the determining step may further comprise determining when the pressure comprises the selected negative pressure based at least in part on the electrical current drawn by the actuator device when retracting the piston member.

In other embodiments, the actuator device may comprise a hydraulic servo system comprising a hydraulic actuator for extending the piston member toward the distal end and retracting the piston member toward the proximal end. In such embodiments, the output of the actuator device may comprise a hydraulic pressure within the hydraulic actuator when retracting the piston member. Furthermore, according to some such embodiments, the determining step may further comprise determining when the pressure comprises the selected negative pressure based at least in part on the hydraulic pressure within the hydraulic actuator when retracting the piston member.

In some method and/or computer program product embodiments, the providing step may further comprise providing an indicia comprising a perceptible output transmitted via a user interface. In such embodiments, the perceptible output may include, but is not limited to an audible alarm and a visible indicia. Furthermore, in some method and/or computer program embodiments, the providing step may further comprise providing an indicia comprising a prompt to clear an obstruction in a conduit in fluid communication with and disposed distally from the dispensing aperture. Such a prompt may include, but is not limited to text instructions and a pictogram.

Thus, the various embodiments of the present invention provide many advantages that may include, but are not limited to: advising a user of the injector device when a potentially hazardous vacuum condition is produced in a syringe device operably engaged with the injector device; providing for the automatic shut-off of the injector device when a negative pressure within the syringe indicates that a distal dispensing end of the syringe is occluded; preventing unchecked and/or inadvertent retraction of a plunger device that may allow for cross-contamination of multiple-syringe injector devices; preventing inadvertent production of potentially embolic air or vapor bubbles in a syringe device; and providing a prompt to a user of an injector device to remove occlusions located distally from the syringe device so as to reduce the chance of producing a potentially-hazardous vacuum condition within the syringe.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1a is a non-limiting schematic of an injector system, according to one embodiment of the present invention, wherein the actuator device comprises an electric motor operably engaged with a movable plunger head configured to be selectively operably engaged with the piston member of a syringe device;

FIG. 1b is a non-limiting schematic plot of current versus retraction distance generated by a controller device, according to one embodiment of the injector system of the present invention;

Figure 7:
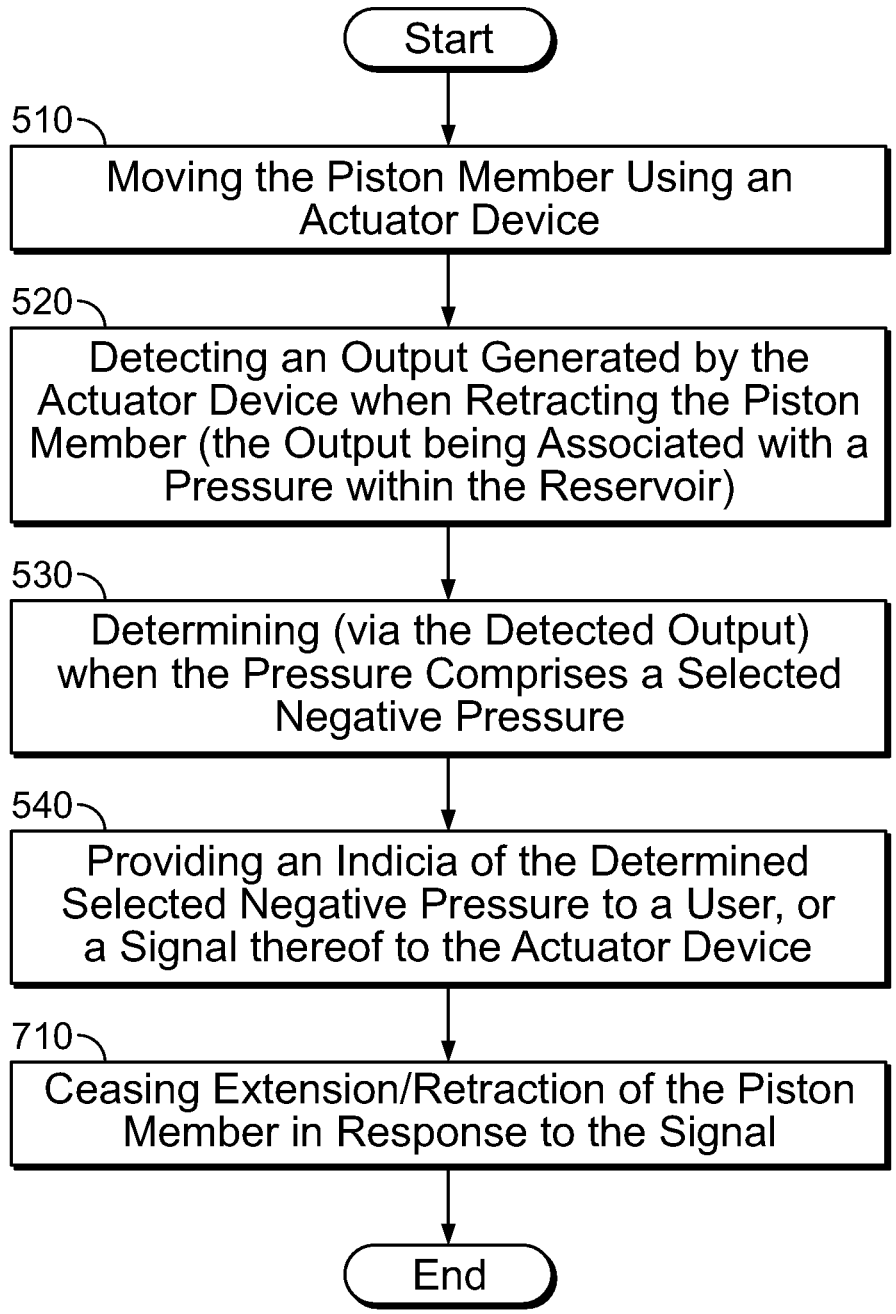
Figure 8:
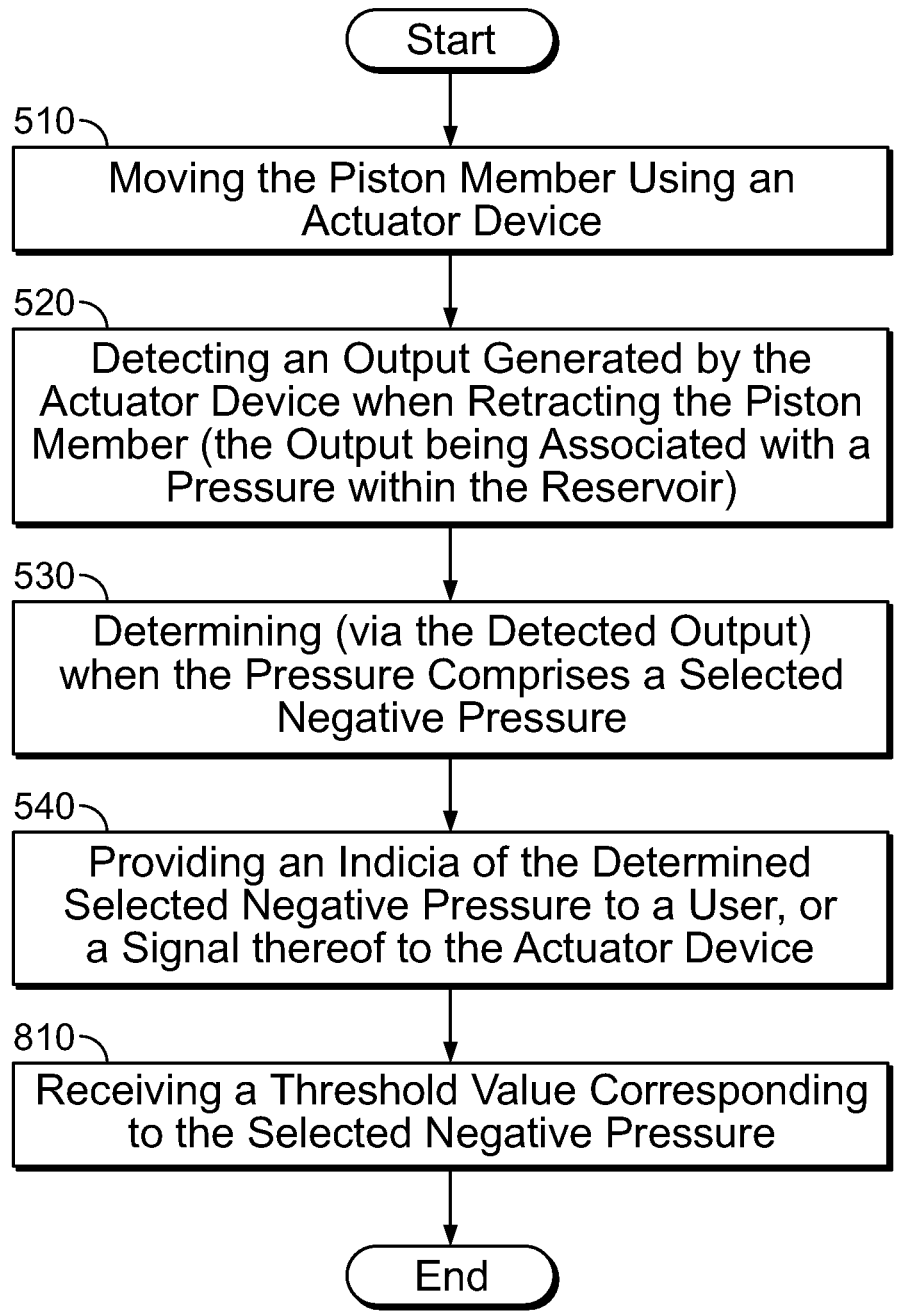

FIG. 7 is a non-limiting flow chart schematic of a method for detecting a substantially negative pressure in a syringe device, according to one embodiment of the present invention including a step for ceasing extension and/or retraction of a piston member in response to a provided signal; and FIG. 8 is a non-limiting flow chart schematic of a method for detecting a substantially negative pressure in a syringe device, according to one embodiment of the present invention including a step for receiving a threshold value corresponding to a selected negative pressure within a syringe device.

DETAILED DESCRIPTION OF VARIOUS EMBODIMENTS OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figures 2A, 2B:
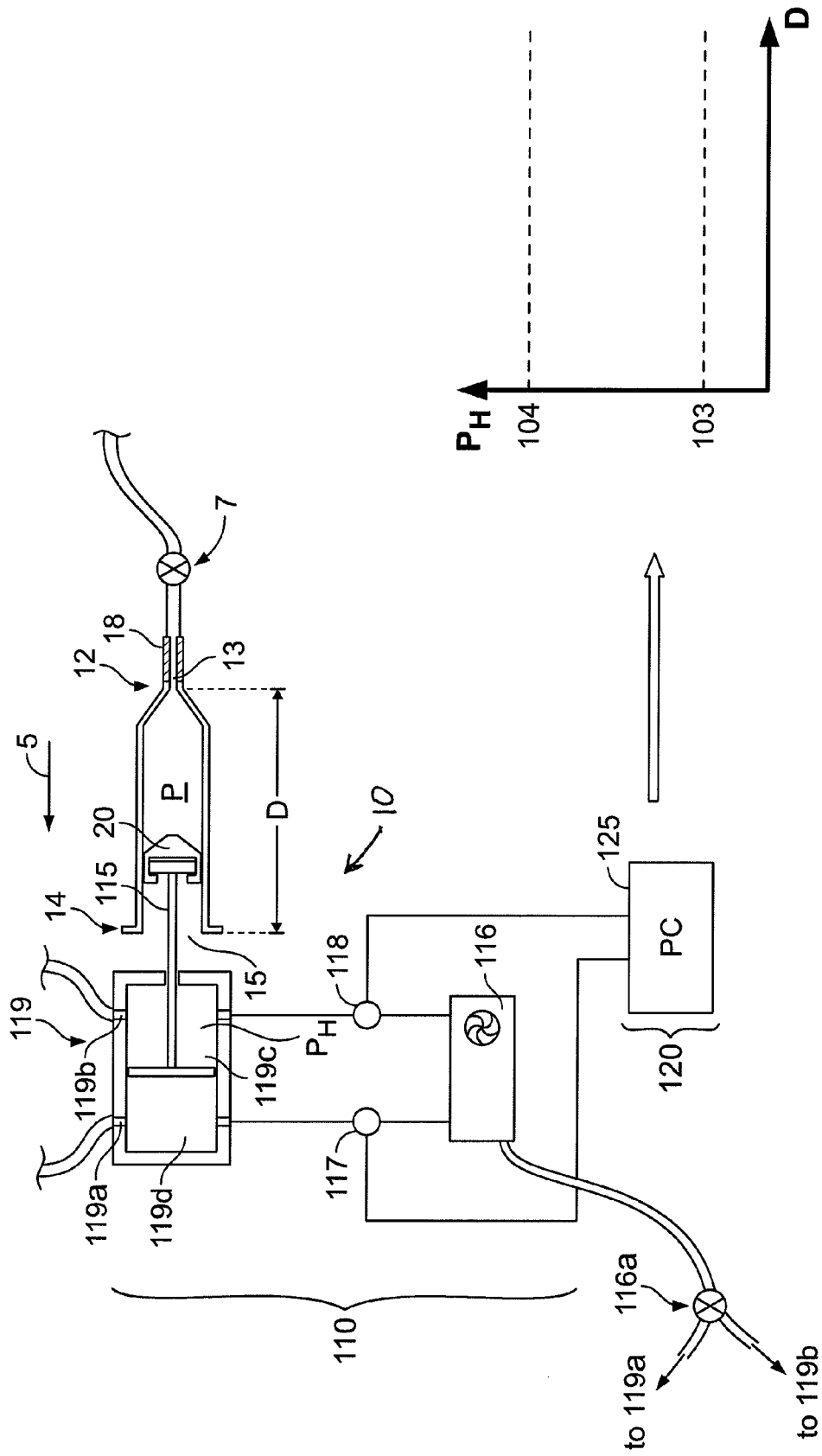
FIG. 2a is a non-limiting schematic of an injector system, according to one embodiment of the present invention, wherein the actuator device comprises a hydraulic servo system comprising a hydraulic actuator for extending and retracting the piston member of a syringe device.
FIG. 2b is a non-limiting schematic plot of hydraulic pressure versus retraction distance generated by a controller device, according to one embodiment of the injector system of the present invention.
Figure 4:
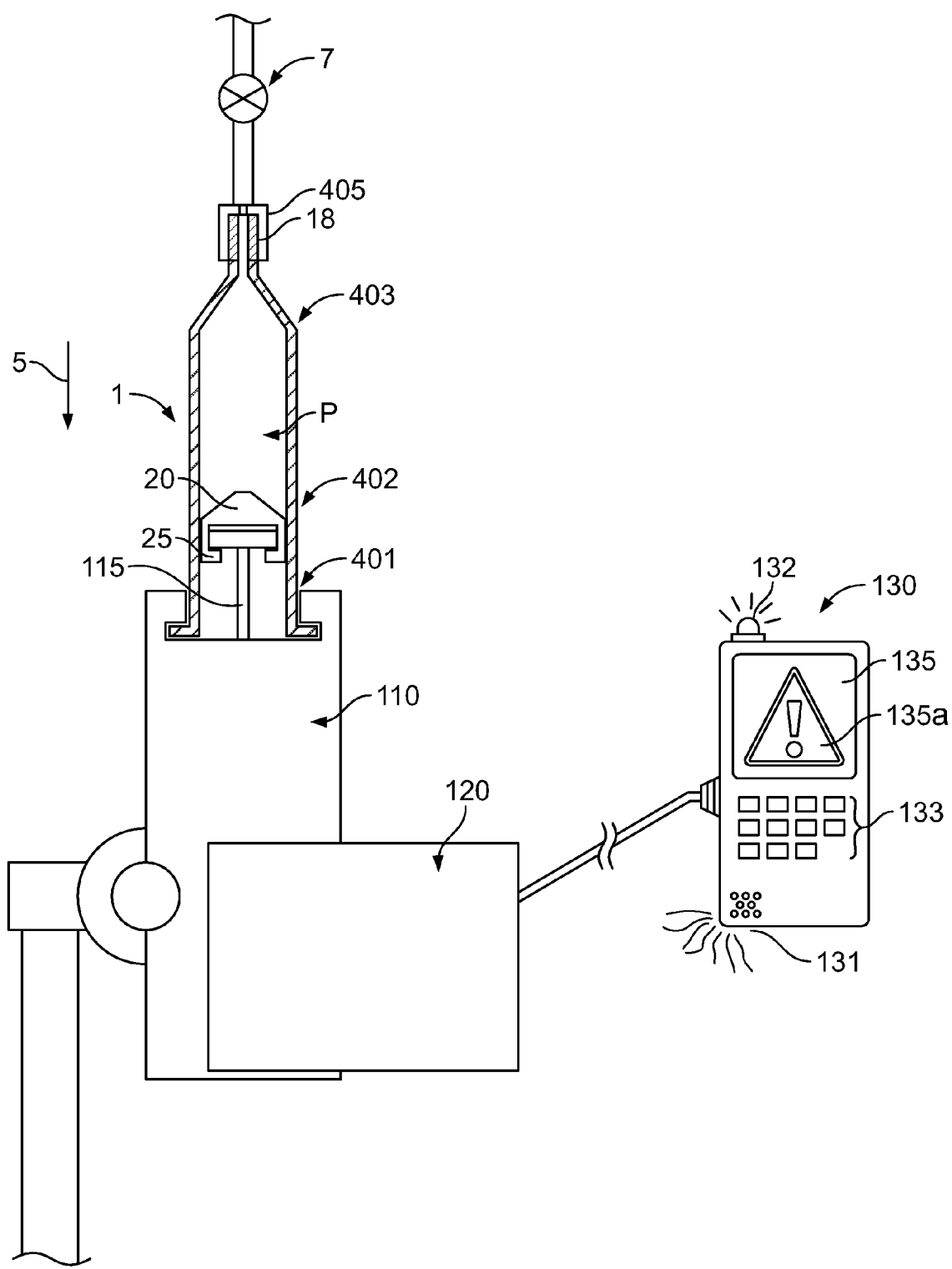
FIG. 4 is a non-limiting schematic of an injector system, according to one embodiment of the present invention, comprising a user interface in communication with the controller device.
Figure 5:
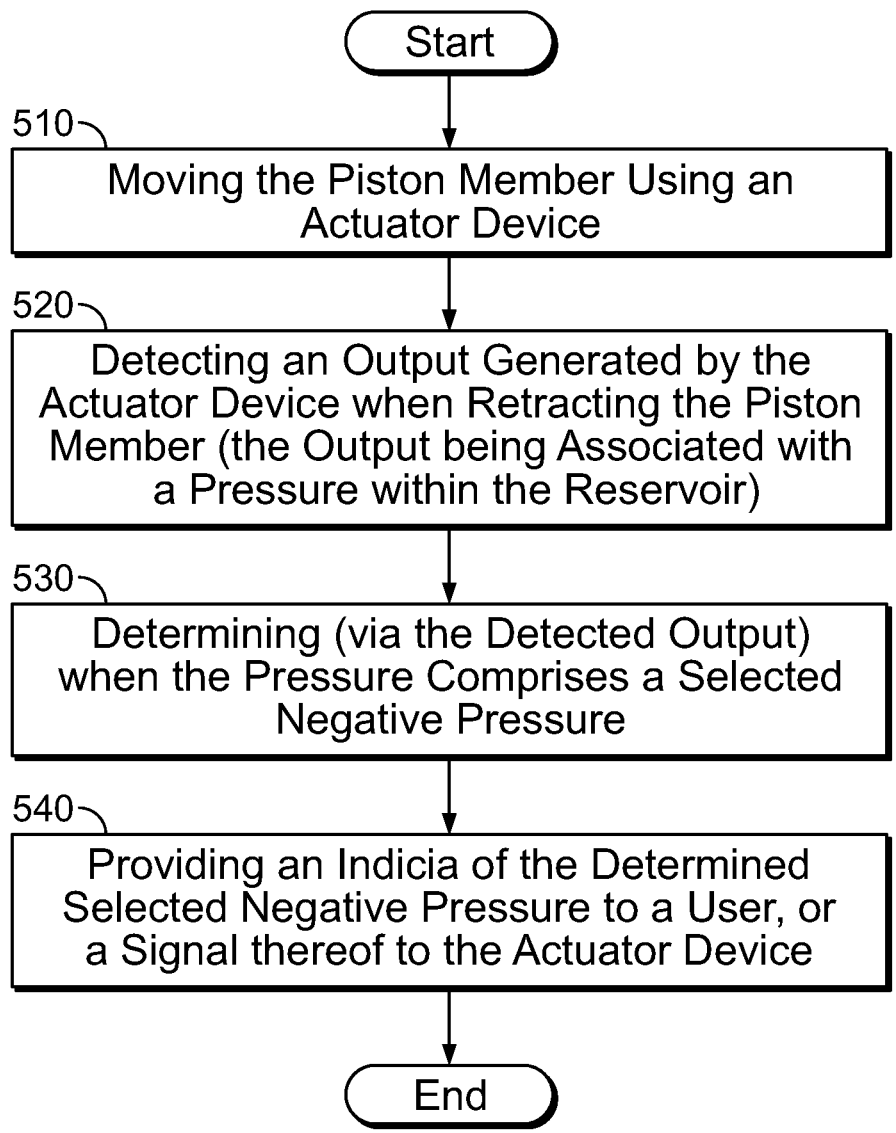
FIG. 5 is a non-limiting flow chart schematic of a method for detecting a substantially negative pressure in a syringe device, according to one embodiment of the present invention.

While the injector system 1 embodiments discussed herein and shown generally in FIGS. 1a, 2a, and 4 are discussed in the context of a single actuator device 110 (and a corresponding single syringe device 1 operably engaged therewith), it should be understood that various embodiments of the present invention may provide a controller device 120 (and/or multiple controller devices 120 in communication with one another, for example) that may be configured to be capable of monitoring the outputs (current I and hydraulic pressure $P_H$ within an actuator device 110, for example) of multiple actuator devices 110. Thus, the various system, method, and computer program product embodiments herein may be used to detect selected negative pressures within syringe devices 1 that may be indicative of movement (in the retraction direction 5, for example) of one or more piston members 20 in a plurality of syringe devices 1. Thus, various embodiments described herein may be used to detect retraction in one or more of the plurality of syringe devices 1 that may lead to cross-contamination in injector systems having multiple syringe devices 1 operably engaged therewith (via a central manifold, for example).

FIGS. 1a and 2a show an injector system 10 according to one embodiment of the present invention wherein the injector system 10 is adapted to be operably engaged with a syringe device 1 comprising a reservoir including a dispensing distal end 12 defining a dispensing aperture 13 and a proximal end 14 defining a proximal aperture 15. The syringe device 1 may further comprise a piston member 20 movably disposed in the reservoir and configured to be movable between the distal end 12 and the proximal end 14 of the syringe device 1 (i.e. to some point along the distance D defined between the proximal end 14 and the dispensing distal end 12 of the syringe device 1). The piston member 20 may be in movable sealing engagement with a reservoir sidewall of the syringe device 1 such that a substantially fluid-tight seal is present between the piston member 20 and a sidewall of the syringe device 1. As described further herein, the injector system 10 may be adapted to be operably engaged with a variety of different types of syringe devices including, but not limited to a syringe device defining a vent for relieving a vacuum in the syringe device 1, such as that disclosed generally in U.S. patent application Ser. No. 11/539,805, entitled Syringe Device and Injector System including a Vent for Relieving a Vacuum within a Syringe, which is hereby incorporated by reference herein in its entirety.

In one embodiment, as shown generally in FIG. 1a, the injector system 10 may comprise an actuator device 110 configured to be selectively operably engaged with the piston member 20 for extending the piston member 20 toward the distal end 12 of the syringe device 1 and retracting the piston member 20 toward the proximal end 14 of the syringe device 1. The injector system 10 may further comprise a controller device 120 in communication with the actuator device 110, wherein the controller device 120 is configured to detect an output generated by the actuator device 110 when retracting the piston member 20. The output may be associated with a pressure P within the reservoir of the syringe device 1. For example, as described further herein with respect to FIGS. 3a and 3b, the output (such as a current I drawn by an actuator device 110 comprising an electric motor 111 (see FIG. 1) and/or a hydraulic pressure $P_H$ within an actuator device 110 comprising a hydraulic actuator 119 (see FIG. 2) may be linearly related to a pressure P within the reservoir of the syringe device 1.

According to some embodiments, the controller device 120 may be further configured to determine, via the detected output (including but not limited to an electrical current I and/or a hydraulic pressure $P_H$ within an actuator device 110 comprising a hydraulic actuator 119), when the pressure P comprises a selected negative pressure and to provide an indicia thereof to a user (via a user interface 130, for example, as shown in FIG. 4) or a signal thereof to the actuator device 110, in response to the determined selected negative pressure. In some embodiments, the controller device 120 may be further configured to be capable of converting the output (including but not limited to an electrical current I and/or a hydraulic pressure $P_H$ within an actuator device 110 comprising a hydraulic actuator 119) into a pressure value P comparable to the selected negative pressure (see, for example, the hydraulic pressure $P_H$ threshold values 103, 104 illustrated in FIG. 2b). As described further herein, some injector system 10 embodiments may further comprise a user interface 130 (see FIG. 4, for example) configured to receive a threshold value (see, for example threshold current I values 101, 102 and threshold hydraulic pressure $P_H$ values 103, 104 plotted against a distance D in FIGS. 1b and 2b) corresponding to the selected negative pressure (via the relationships shown generally in FIGS. 3a and 3b, for example). As shown generally in FIGS. 1b and 2b, the controller device 120 may be configured to be capable of plotting the output during an extension and/or retraction cycle (i.e. when moving the piston member 20 in the retraction direction 5) versus a distance D along a length of the syringe device 1. The characteristic plots of the outputs (see FIGS. 1b and 2b, which may include, but are not limited to an electrical current I and/or a hydraulic pressure $P_H$ within an actuator device 110 comprising a hydraulic actuator 119) may be converted (by the controller device 120, for example) into corresponding plots of the pressure P in the syringe device 1 (which may correspond, for example, to a selected negative pressure generally indicative of a vacuum condition produced within the syringe device 1 during a retraction cycle).

Figure 3A:
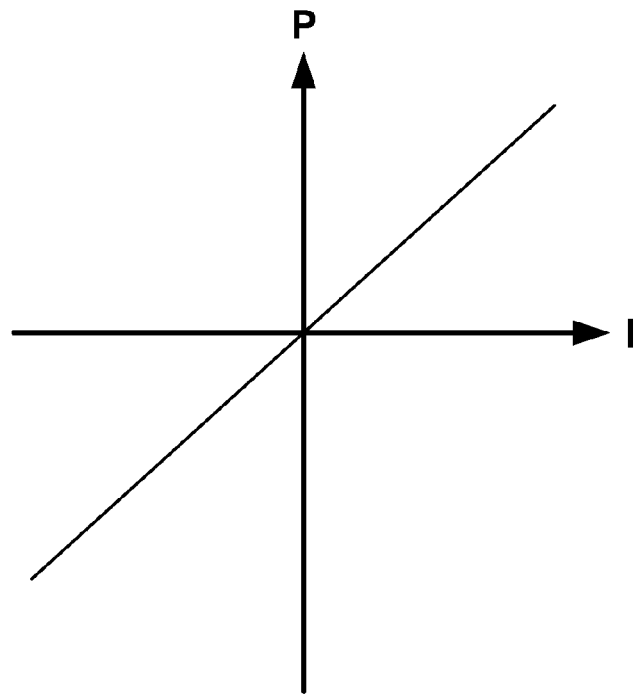
FIG. 3a is a non-limiting schematic plot of pressure (P) in a syringe device versus current (I) drawn by an actuator device comprising an electric motor, according to one embodiment of the injector system of the present invention.
Figure 3B:
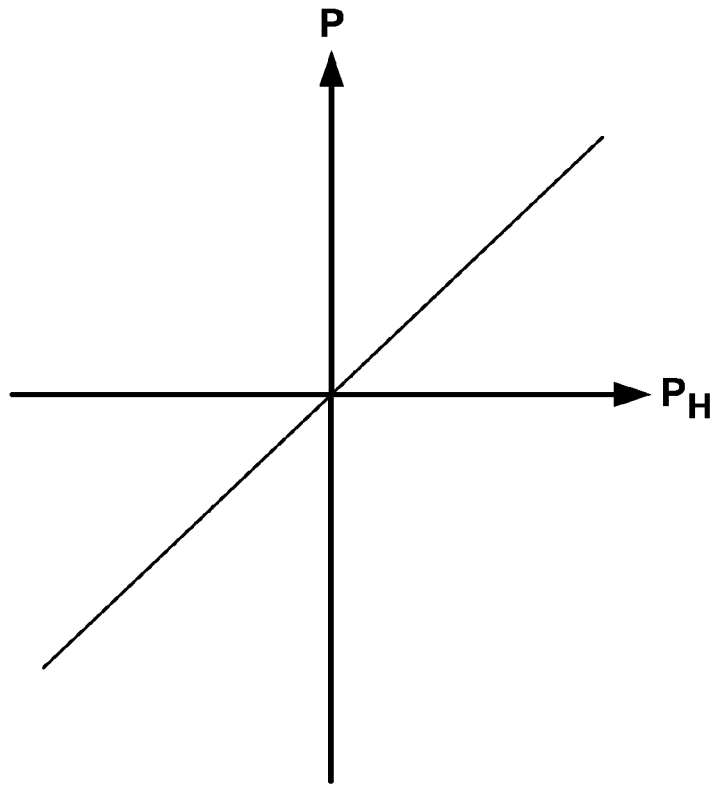
FIG. 3b is a non-limiting schematic plot of pressure (P) in a syringe device versus hydraulic pressure ($P_H$) in an actuator device comprising a hydraulic actuator, according to one embodiment of the injector system of the present invention.

For example, in some embodiments, the controller device 120 may comprise a computer device 125 (including a memory device, for example) capable of converting the output into a pressure value P using the relationships shown schematically in FIGS. 3a and 3b. While the relationships between the outputs (I and $P_H$, for example) and the pressure P within the syringe device 1 are shown in FIGS. 3a and 3b are generally linear such that a given output may be converted to a corresponding pressure P using a single slope factor, it should be understood that the controller 120 (and/or a computer device 125 thereof) may be further configured to be capable of storing output relationships to the syringe device 1 pressure P that may include, but are not limited to a variety of linear and non-linear mathematical functions such that the controller 120 may be capable of converting the output into the pressure P. As shown in FIGS. 1b and 2b the controller device 120 may comprise a computer device 125 configured to be capable of generating one or more output thresholds 101, 102, 103, 104 that may correspond to the selected negative pressure (via the linear relationships shown in FIGS. 3a and 3b, for example).

In some embodiments the output may comprise an electrical current I drawn by the actuator device 110 when retracting the piston member 20. As shown in FIG. 1a, the actuator device 110 may comprise an electric motor 111 operably engaged with a movable plunger head 115 configured to be selectively operably engaged with the piston member 20 for extending the piston member 20 toward the distal end 12 of the syringe device 1 and retracting the piston member 20 toward the proximal end 14 of the syringe device 1. The electric motor 110 may be operably engaged with the movable plunger head 115 via one or more drive elements that may include, but are not limited to: a drive belt 112; a gear set 113; and a jack screw 114 (which may be configured to convert the rotary movement of the electric motor 110 into the substantially linear motion of the moveable plunger head 115.) The electric motor 111 may comprise an induction device and/or stepper motor in communication with a linear circuit 121 that may serve as a component of the controller device 120 described further herein.

According to some such embodiments, the output of the actuator device 110 may comprise an electrical current I drawn by the actuator device 110 when retracting the piston member 20 (i.e. when moving the piston member 20 in the retraction direction 5). Furthermore, and as shown in FIG. 1, the system 10 may comprise a controller device 120 comprising an electrical sensor 122 (such as an analog/digital converter, for example) configured to determine when the pressure P comprises the selected negative pressure based at least in part on the electrical current I drawn by the actuator device 110 when retracting the piston member 20. As shown in FIG. 1a, the electrical sensor 122 may be operably engaged with a linear circuit 121 in a substantially parallel relationship with a resistance element R having a selected resistance value. The electrical sensor 122 may be configured to be capable of determining (based at least in part on the voltage drop across the resistance element R and the selected resistance value thereof) the current I drawn by the actuator device 110 when moving the piston member 20 in the retraction direction 5. As shown in FIG. 1b, the selected negative pressure may be converted automatically (by the computer device 125 of the controller device 120, for example) into a corresponding current threshold 102 such that the controller device 120 may be capable of providing an indicia of the determined selected negative pressure to a user (via a user interface 130 (see FIG. 4) and/or providing a signal thereof to the actuator device 110. As described further herein, the actuator device 110 may be responsive to the signal and may be configured to be capable of ceasing extension of the piston member 20 and/or retraction of the piston member 20 in the retraction direction 5 in response to the signal.

In other system 10 embodiments, as shown generally in FIG. 2a, the output may comprise a hydraulic pressure $P_H$ within the actuator device 110 (comprising a hydraulic actuator 119, for example) when retracting the piston member 20. For example, in such embodiments, the actuator device 110 may comprise a hydraulic servo system comprising a hydraulic actuator 119 for extending the piston member 20 toward the distal end 12 of the syringe device 1 and retracting the piston member 20 toward the proximal end 14 of the syringe device 1. According to some such embodiments, the hydraulic actuator 119 may comprise a hydraulic cylinder defining an extension chamber 119d and a retraction chamber 119c. The hydraulic actuator 119 may further define one or more fluid apertures 119a, 119b in communication with a source of hydraulic fluid (such as a hydraulic fluid sump or reservoir (not shown) in fluid communication with a pump device 116 for conveying the hydraulic fluid to and from the chambers 119c, 119d of the hydraulic actuator 119. As shown in FIG. 2a, the pump device 116 may be in fluid communication with an outlet tube comprising a valve device 116a for directing a flow of hydraulic fluid to at least one of the fluid apertures 119a, 119b so as to fill at least one of the extension chamber 119d and the retraction chamber 119c with hydraulic fluid so as to move the movable plunger head 115 in at least one of the extension direction and the retraction direction 5.

According to some such embodiments, the output of the actuator device 110 may comprise a hydraulic pressure $P_H$ within the hydraulic actuator 119 when retracting the piston member 20 (i.e. moving the piston member 20 in the retraction direction 5 via the movement of the movable plunger head 115, for example). According to such embodiments, the controller device 120 may comprise a pressure transducer device 118 (see also element 117, denoting a pressure transducer device in communication with the extension chamber 119d of the hydraulic actuator 119) configured to determine when the pressure P comprises the selected negative pressure based at least in part on the hydraulic pressure $P_H$ within the hydraulic actuator 119 (and more particularly, in the retraction chamber 119c thereof) when retracting the piston member 20. As shown in FIG. 2a, the pressure transducer devices 117, 118 may be in communication with the controller device 120 (which may comprise, for example, a computer device configured to be capable of converting the detected hydraulic pressure $P_H$ within the hydraulic actuator 119 when retracting the piston member 20 into a corresponding pressure P within the syringe device 1 during a retraction cycle). As shown in FIG. 2b, the selected negative pressure may be converted automatically (by the computer device 125 of the controller device 120, for example) into a corresponding hydraulic pressure threshold 104 such that the controller device 120 may be capable of providing an indicia of the determined selected negative pressure to a user (via a user interface 130 (see FIG. 4) and/or providing a signal thereof to the actuator device 110. As described further herein, the actuator device 110 may be responsive to the signal and may be configured to be capable of ceasing extension of the piston member 20 and/or retraction of the piston member 20 in the retraction direction 5 in response to the signal.

As shown in FIG. 4, the injector system 10 may further comprise a user interface 130 in communication with the controller device 120. In some embodiments, the user interface 130 may comprise a keypad 133 and/or a display 135 comprising a touch-screen feature configured to receive a threshold value (including, but not limited to: a threshold pressure P, a threshold current I value 102 (see FIG. 1b), and a threshold hydraulic pressure $P_H$ value 104 (see FIG. 2b), corresponding to the selected negative pressure.

Furthermore, in some embodiments, the user interface 130 may comprise a display 135, speaker 131, and/or an indicator light 132 configured to be capable of producing an indicia of the determined selected negative pressure comprising a perceptible output transmitted via the user interface 130 such that a user may be made aware when the pressure P within the syringe device 1 approaches and/or exceeds the selected negative pressure. As discussed further herein, the selected negative pressure may correspond to one or more threshold values (such as, for example, a current I threshold value 102 (see FIG. 1b) and/or a hydraulic pressure $P_H$ threshold value 104 (see FIG. 2b). According to some embodiments, the user interface 130 may comprise a speaker 131 and the perceptible output may comprise an audible alarm transmitted via the speaker 131. Furthermore, in some embodiments, the user interface 130 may comprise a display 135 and the perceptible output may comprise a visible indicia 135a transmitted via the display 135.

In some injector system 10 embodiments comprising a user interface 130 having a display 135, the visual indicia 135a transmitted to the user via the display 135 may comprise a prompt to clear an obstruction (such as a closed check valve 7, for example) in a conduit in fluid communication with the dispensing aperture 13 of the syringe device 1. According to various embodiments, the prompt may include, but is not limited to: text instructions for clearing the obstruction (such as, for example, instructions on how to open a closed check valve 7); a pictogram (including, for example, non-text instructions for clearing the obstruction distal from the dispensing aperture 12 of the syringe device 1); and/or combinations of such visual indicia 135a. Furthermore, in some injector system 10 embodiments, the user interface 130 may comprise an indicator light 132 configured to be capable of illuminating to provide the visual indicia to the user when the controller device 120 has detected a pressure P approaching and/or exceeding the selected negative pressure in the syringe device 1.

As described generally herein, the controller device 120 may be configured to be capable of determining, via the detected output (such as current I and/or hydraulic pressure $P_H$ for example), when the pressure P within the syringe device 1 comprises a selected negative pressure and to provide a signal thereof to the actuator device 110, in response to the determined selected negative pressure. According to some such embodiments, the controller device 120 may be in communication with the actuator device 110 in a feedback loop or other control arrangement such that the actuator device 110 is further configured to automatically cease extending the piston member 20 toward the distal end 12 of the syringe device and/or cease retracting the piston member 20 toward the proximal end 14 of the syringe device 1 in response to the signal provided by the controller device 120. Thus, by entering a selected negative pressure and/or a threshold 102, 104

(corresponding to a maximum desired current I or hydraulic pressure $P_H$, for example), a user may select a threshold pressure P that when detected within the syringe device 1, may trigger the automatic shutdown of the actuator device 110. Such automatic shutdown features may, in some embodiments, reduce and/or minimize the generation of vacuum and/or excessive negative pressure P within the syringe device 1 when retracting the piston member 1.

FIGS. 4-8 illustrate various method embodiments for detecting a substantially negative pressure in a syringe device 1 (see, FIG. 1a, for example) comprising a reservoir including a dispensing distal end 12 defining a dispensing aperture 13 and a proximal end 14 defining a proximal aperture 15. As described herein with respect to the various injector system 10 embodiments, the syringe device 1 may further comprise a piston member 20 movably disposed in the reservoir and configured to be movable between the distal end 12 and the proximal end 14. The piston member 20 may be in movable sealing engagement with a reservoir sidewall. As shown generally in FIG. 5, the method may comprise step 510 for moving the piston member 20 using an actuator device 110 configured to be selectively operably engaged with the piston member 20 (via a movable plunger head 115, for example) for extending the piston member 20 toward the distal end 12 of the syringe device 1 and retracting the piston member 20 toward the proximal end 14 of the syringe device 1. Such method embodiments, may further comprise step 520 for detecting an output (such as, for example, a current I drawn by the actuator device 110 when moving the piston member 20 in the retraction direction 5 and/or a hydraulic pressure $P_H$ detected in the retraction chamber 119c of the hydraulic actuator 119 (shown in FIG. 2a, for example)). As shown generally in FIGS. 3a and 3b, the various outputs may be associated with a pressure P within the reservoir of the syringe device 1. Furthermore, various method embodiments may further comprise step 530 for determining, via the detected output, when the pressure P comprises a selected negative pressure (that may be indicative, for example, of the production of a substantial vacuum within the syringe device 1 (particularly if a distal check valve 7 is closed when moving the piston member 20 in the retraction direction 5). Some method embodiments further comprise step 540 for providing an indicia of the determined selected negative pressure to a user or a signal thereof to the actuator device 110, as described further herein.

In some method and/or computer program product embodiments, step 540 for providing indicia of the determined selected negative pressure to a user may comprise providing indicia comprising a perceptible output transmitted via a user interface 130. As described herein, the user interface 130 may be integrated with and/or in communication with the controller device 120. Furthermore, the user interface 130 may comprise at least one of a display 135, a speaker 131, and an indicator light 132 for providing an indicia of the selected negative pressure (as determined, for example, in step 530) to a user. Thus, in some embodiments, step 540 may comprise providing a perceptible output comprising an audible alarm (generated, for example, by a speaker 131). In some method embodiments, step 540 may comprise providing a perceptible output comprising a visible indicia 135a, which may be generated, by various components of a user interface 130 including, but not limited to: an indicator light 132 and a display 135. For example, in some embodiments, step 540 further comprises providing a visible indicia 135a comprising a prompt to clear an obstruction (such as a closed check valve 7, for example) in a conduit in fluid communication with the dispensing aperture 13 of the syringe device 1 (which, as described herein, may serve to at least partially relieve a vacuum or negative pressure produced within the syringe device 1 when moving the piston member 20 in the retraction direction 5). According to such embodiments, the visual indicia 135a may comprise a prompt that includes, but is not limited to text instructions and a pictogram instructing a user on how to clear the obstruction and/or otherwise relieve the negative pressure within the syringe device 1.

As shown in FIG. 8, some method embodiments may further comprise step 810 for receiving a threshold value (that may include, for example, a threshold current I value 102 (see FIG. 1b) and/or a threshold hydraulic pressure $P_H$ value 104 (see FIG. 2b) corresponding to a selected negative pressure. Furthermore, in some embodiments, the threshold value received in step 810 may comprise a selected negative pressure value that may be converted (in step 610, for example) into an output value that may be directly comparable to the output detected in step 520. As discussed herein with respect to various injector system 10 embodiments, the various actuator device 110 outputs (such as current I and/or hydraulic pressure $P_H$) may be readily converted into corresponding pressure P values using known mathematical relationships such as the substantially linear plots of output values versus pressure P in the syringe device 1. As discussed herein, various injector system 10 embodiments may comprise a user interface 130 including a keypad 133 (see FIG. 4, for example) and/or a display 135 (which may comprise a touchscreen display) such that a user may enter a threshold value and/or select a predetermined threshold value that may trigger the provision of an indicia and/or signal as part of step 540.

Figure 6:
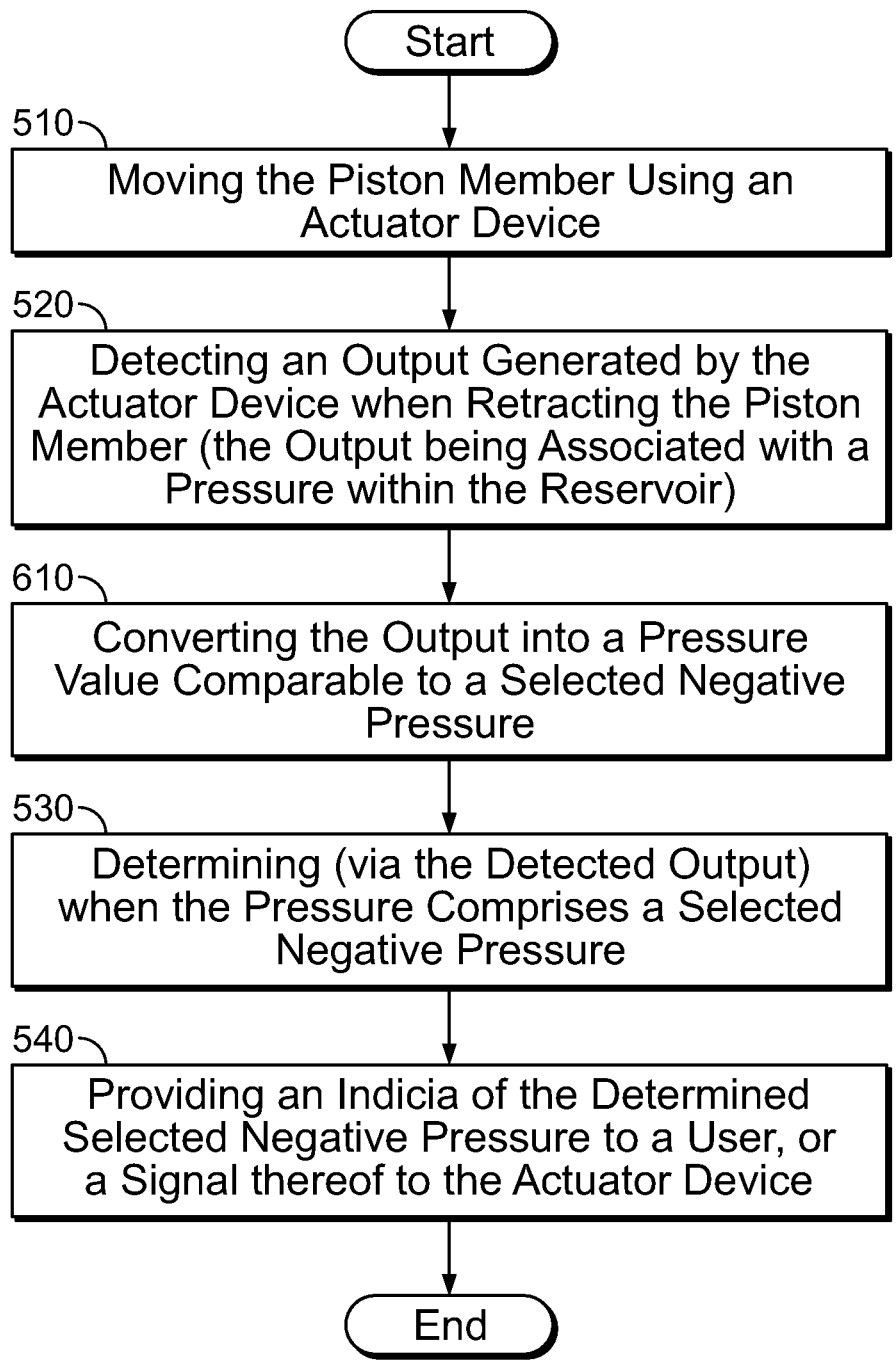
FIG. 6 is a non-limiting flow chart schematic of a method for detecting a substantially negative pressure in a syringe device, according to one embodiment of the present invention including a step for converting an output into a pressure value comparable to a selected negative pressure.

As shown in FIG. 6, some method embodiments may further comprise step 610 for converting the output (such as the current I drawn by the actuator device 110 or a hydraulic pressure $P_H$ detected in the retraction chamber 119c of the hydraulic actuator 119, for example) into a pressure value P (within the syringe device 1, for example) that may be comparable to the selected negative pressure. As shown generally in FIGS. 3a and 3b, step 610 may be accomplished by consulting one or more plots of the output versus pressure P in the syringe device 1. While FIGS. 3a and 3b indicate a generally linear relationship between current I drawn by the actuator device 110 or a hydraulic pressure $P_H$ detected in the retraction chamber 119c of the hydraulic actuator 119 and the pressure P within the syringe device 1, it should be understood that other mathematical relationships between the outputs (current I and hydraulic pressure $P_H$, for example) and the pressure P within the syringe device 1 may be generated based on the configuration of the injector system 1 and various components thereof. Thus, step 610 may be performed by a controller device 120 (and/or a computer device 125 thereof) in communication with the actuator device 110 in order to generate a pressure value P that may be directly comparable to a pressure threshold value entered by a user, for example. It should be further understood, that a given pressure threshold (entered by a user via a user interface 130 as part of step 810 discussed herein, for example) may also be converted (using linear and/or other mathematical relationships between the outputs I, $P_H$ and the pressure P), to a corresponding current threshold 102 (see FIG. 1b, for example) and/or hydraulic pressure threshold 104 (see FIG. 2b, for example).

As described herein with respect to various injector system 10 embodiments (see FIG. 1a, for example), the actuator device 110 may comprise an electric motor 111 operably engaged with a movable plunger head 115 configured to be selectively operably engaged with the piston member 20 for extending the piston member 20 toward the distal end 12 and retracting the piston member 20 toward the proximal end 14. According to such embodiments, the output of the actuator device 110 may comprise an electrical current I drawn by the actuator device 110 when moving the piston member 20 in the retraction direction 5. Furthermore, according to such embodiments, the determining step 530 may further comprise determining when the pressure P within the syringe device 1 comprises the selected negative pressure based at least in part on the electrical current I drawn by the actuator device 110 when retracting the piston member 20. In such embodiments, the converting step 610 may be performed, for example, by the controller device 120 using a known linear relationship between the output electrical current I and the pressure P within the syringe device 1 as shown schematically in FIG. 3a, for example.

Furthermore, in some embodiments, the actuator device 110 may comprise a hydraulic servo system comprising a hydraulic actuator 119 (in fluid communication with a pump 116 and valve 116a, for example) for extending and/or retracting the piston member 20 within the syringe device 1. According to some such embodiments, the output of the actuator device 110 (as detected by one or more pressure transducers 117, 118 in fluid communication with the hydraulic actuator 119) may comprise a hydraulic pressure $P_H$ within the hydraulic actuator 119 (and/or within a retraction chamber 119c thereof) when retracting the piston member 20. According to such embodiments, the determining step 530 may further comprise determining when the pressure P comprises the selected negative pressure based at least in part on the hydraulic pressure $P_H$ within the hydraulic actuator 119 (and/or within a retraction chamber 119c thereof) when moving the piston member 20 in the retraction direction 5. In such embodiments, the converting step 610 may be performed, for example, by the controller device 120 using a known linear relationship between the output hydraulic pressure $P_H$ (as detected by one or more pressure transducers 117, 118 in fluid communication with the hydraulic actuator 119) and the pressure P within the syringe device 1 as shown schematically in FIG. 3b, for example.

FIG. 7 shows an additional method embodiment comprising step 710 for ceasing extension of the piston member 20 toward the distal end 12 of the syringe device 1 or ceasing retraction of the piston member 20 (in the retraction direction 5) toward the proximal end 14 of the syringe device) in response to the signal provided (by the controller device 120, for example) to the actuator device 110 in step 540. Thus, as described herein with respect to various injector system 10 embodiments, the actuator device 110, in step 710 may be responsive to the signal generated by a controller device 120 as part of step 540 for providing a signal of the determined selected negative pressure in the syringe device 1. More particularly, in some method embodiments, the actuator device 110 may be configured to cease movement of the piston member 20 in the retraction direction 5 in response to the signal (which may indicate that a potentially hazardous negative pressure is being produced in the syringe device during a particular retraction cycle). Thus, step 710 for ceasing retraction of the piston member 20 may provide a pause in which a user may respond to one or more of the indicia (provided in some embodiments by a user interface 130) produced in step 540 that may include prompts to clear an obstruction distal to the syringe device 1 and/or other indicia prompting a user to substantially relieve the negative pressure produced within the syringe device 1 before resuming the retraction cycle.

In addition to providing injection systems 1 and methods, the embodiments herein also provide computer program products for performing the operations described above. The computer program products have a computer readable storage medium having computer readable program code means embodied in the medium. With reference to FIGS. 1a, 2a, and 4, the computer readable storage medium may be part of the controller device 120 (and/or a computer device 125 in communication therewith and/or integrated therein) and may implement the computer readable program code means to perform the above discussed operations.

In this regard, FIGS. 5-8 are block diagram illustrations of methods, systems and program products according to the invention. It will be understood that each block or step of the block diagram and combinations of blocks in the block diagram can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer (such as computer device 125, for example) or other programmable apparatus to function in a particular manner, such that the instructions stored in the computer-readable memory produce an article of manufacture including instructions which implement the various steps and/or functions specified in the block diagram, flowchart or control flow block(s) or step(s). The computer program instructions may also be loaded onto a computer or other programmable apparatus to cause a series of operational steps to be performed on the computer or other programmable apparatus (for example, the controller 120 and/or an actuator device 110 in communication therewith) to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of steps for performing the specified functions and program instructions for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An injector system adapted to be operably engaged with a syringe device, the syringe device comprising a reservoir including a dispensing distal end defining a dispensing aperture and a proximal end defining a proximal aperture, the syringe device further comprising a piston member movably disposed in the reservoir and configured to be movable between the distal end and the proximal end, the piston member being in movable sealing engagement with a reservoir sidewall, the injector system comprising:

an actuator device comprising an electric motor operably engaged with a movable plunger head, the actuator device configured to be selectively operably engaged with the piston member for extending the piston member toward the distal end and retracting the piston member toward the proximal end; and a controller device in communication with the actuator device, the controller device being configured to detect an output generated by the actuator device when retracting the piston member, the output of the actuator device comprises an electrical current drawn by the actuator device when retracting the piston member, the output being associated with a pressure within the reservoir, the controller device comprising an electrical sensor configured to determine, via the detected output, when the pressure within the reservoir comprises a selected negative pressure based at least in part on the electrical current drawn by the actuator device when retracting the piston member, the controller device being configured to provide a signal thereof to the actuator device, in response to the selected negative pressure, wherein the actuator device is further configured to automatically cease retracting the piston member during the retraction of the piston member toward the proximal end in response to the signal provided by the controller device when negative pressure detected within the reservoir reaches the selected negative pressure during retraction of the piston member.

2. An injector system according to claim 1, wherein the controller device is further configured to convert the output into a pressure value comparable to the selected negative pressure.

3. An injector system according to claim 1, further comprising a user interface in communication with the controller device, wherein the controller device is configured to provide an indicia of the selected negative pressure, and wherein the indicia comprises a perceptible output transmitted via the user interface.

4. An injector system according to claim 3, wherein the user interface comprises a speaker and the perceptible output comprises an audible alarm.

5. An injector system according to claim 3, wherein the user interface comprises a display and the perceptible output comprises a visible indicia.

6. An injector system according to claim 5, wherein the visible indicia comprises a prompt to clear an obstruction in a conduit in fluid communication with the dispensing aperture.

7. An injector system according to claim 6, wherein the prompt comprises text instructions.

8. An injector system according to claim 6, wherein the prompt comprises a pictogram.

9. An injector system according to claim 1, further comprising a user interface configured to receive a threshold value corresponding to the selected negative pressure.

* * * * *